United States Patent [19]

Bogart

[11] Patent Number: 5,716,776

[45] Date of Patent: Feb. 10, 1998

[54] ENRICHMENT BY PREFERENTIAL MITOSIS OF FETAL LYMPHOCYTES FROM A MATERNAL BLOOD SAMPLE

[75] Inventor: Mark H. Bogart, 1025 Wilder Ave. #11B, Honolulu, Hi. 96822

[73] Assignee: Mark H. Bogart, Honolulu, Hi.

[21] Appl. No.: 206,484

[22] Filed: Mar. 4, 1994

[51] Int. Cl.⁶ .......................... A01N 1/02; G01N 33/53; G12Q 1/04
[52] U.S. Cl. .................................. 435/2; 436/17; 436/63; 435/7.24; 435/372; 435/377
[58] Field of Search ............... 435/2, 7.24, 372, 435/377; 436/17, 63

[56] References Cited

FOREIGN PATENT DOCUMENTS 9116452  10/1991  WIPO.

OTHER PUBLICATIONS

Merkatz, I.R. et al. (1984) "An association between low maternal serum α-fetoprotein and fetal chromosomal abnormalities" Am. J. Obstet. Gynecol. 148:886–894.

Bogart, M.H. et al. (1987) "Abnormal maternal serum chorionic gonadotropin levels in pregnancies with fetal chromosome abnormalities" Prenat. Diagn. 7:623–630.

Canick, J.A. et al. (1988) "Low second trimester maternal serum unconjugated oestriol in pregnancies with Down's syndrome" Br. J. Obstet. Gynecol. 95:330–333.

Selypes, A., R. Lorencz (1988) "A noninvasive method for determination of the sex and karyotype of the fetus from the maternal blood" Hum. Genet. 79:357–359.

Walknowska, J. et al. (1969) "Practical and theoretical implications of fetal/maternal lymphocyte transfer" The Lancet 1:1119–1122.

Boyer, S.H. et al. (1976) "Enrichment of fetal origin from adult-fetal blood mixtures via selective hemolysis of adult blood cells: an aid to antenatal diagnosis of hemoglobinopathies" Prenat. Diagn. 7:623–630.

Alter, B.P. et al. (1979) "Selective hemolysis of adult red blood cells: an aid to prenatal diagnosis of hemoglobinopathies" Blood 53(2):279–287.

Primary Examiner—Sandra E. Saucier
Attorney, Agent, or Firm—David G. Rosenbaum, Esq.

[57] ABSTRACT

A method is presented for selective stimulation of fetal lymphocytes to divide in culture after treatment of mixed adult-fetal blood samples. This method is particularly useful for diagnosing genetic abnormalities of a fetus using fetal cells from a maternal blood sample. The method consists of preferential destruction of maternal lymphocyte response to low concentrations of mitotic stimulants which results in a relative increase in the number of responding fetal cells in mixed adult-fetal blood samples. In the preferred embodiment of the invention, blood samples from pregnant women are processed by the described methodology, in particular, the erythrocytes are removed from the maternal sample by centrifugation, filtration or preferential lysis with ammonium bicarbonate, the suspension is then subjected to an osmotic shock and exposed to mitotic stimulants in culture, and cells in mitosis are harvested for chromosome analysis. This test will enable detection of fetal chromosome abnormalities by analysis of maternal blood samples.

11 Claims, 3 Drawing Sheets

ENRICHMENT BY PREFERENTIAL MITOSIS OF FETAL LYMPHOCYTES FROM A MATERNAL BLOOD SAMPLE

BACKGROUND OF THE INVENTION

Chromosome abnormalities account for a significant portion of infant morbidity and mortality. In many cases in which a chromosome abnormality is not severe enough to cause death, the baby is mentally retarded—often with the retardation becoming progressively worse. The most common type of chromosomally induced mental retardation is Down's syndrome, the result of an extra number 21 chromosome (trisomy 21), which is observed in one of every 800 live births. The incidence of Down's syndrome (and most other chromosome abnormalities) is an age-related phenomenon showing a rapid increase in incidence with increasing maternal age. For example, at age 29 the incidence is approximately 1 per 1010 births but by age 40 is 1 per 110 live births. This phenomenon is the basis for offering genetic prenatal diagnosis to older pregnant women.

Prenatal diagnosis of chromosome abnormalities is achieved by examination of fetal or placental chromosomes. This can be accomplished by obtaining a small biopsy of the placenta (chorionic villi sampling) or by sampling the amniotic fluid (amniocentesis). Chorionic villi sampling (CVS) is usually performed between 8 to 12 weeks of gestation while amniocentesis is performed from 12 weeks gestation onward. Umbilical cord blood sampling may also be used, but is usually restricted to pregnancies in which there is equivocal data from prior study or a potential fetal abnormality is ascertained during late second or third trimester. Current sampling techniques present some risk to fetal well being and are, therefore, restricted to pregnancies in which the risk of Down's syndrome or other abnormality is sufficiently high to justify the procedure. The risk that is considered "sufficiently high" is arbitrary and has changed over the years. In 1983, the President's Commission for the Study of Ethical Problems in Medicine and Biomedical and Behavioral Science recommended that genetic amniocentesis should be available to all pregnant women.

Current medical standards of care requires physicians to recommend amniocentesis for those women with a Down's syndrome birth risk greater than 1 in 365. This risk rate occurs at the age of 35 and, currently, all women 35 years or older are offered genetic amniocentesis, a test which is close to 100% diagnostic. Unfortunately, genetic amniocentesis is expensive (at an approximate cost of $1,000 per test), time consuming and carries some risk to fetal well being. The risk to the fetus is generally quoted as between 1 in 300 to 1 in 500. Thus, current efforts to detect fetal chromosome abnormalities attempt to balance the risk of a woman having a fetus with abnormality with the risk of procedure-related pregnancy loss.

In the state of California, for example, 9.8% of the babies born each year are born to women that are 35 years of age or older. By offering amniocentesis to these women only about 20 to 25% of all pregnancies with trisomy 21 will be detected (assuming all of the women offered amniocentesis agree to have the testing). This results in 64,860 amniocentesis procedures to detect 347 Down's syndrome fetuses and about 350 other chromosome abnormalities. Somewhere between about 129 and 216 pregnancies are lost as a result of the procedures. Therefore, in recent years there has been considerable effort to improve detection without increasing the number of procedures performed.

Methods for establishing which pregnancies are at highest risk for having a fetus affected with Down's syndrome fall into three categories: epidemiology, biochemical parameters and ultrasound findings. Of these, the epidemiological association between increasing maternal age and increasing incidence of Down's syndrome is the best known. This association forms the basis of offering prenatal diagnosis to women of advance maternal age, usually age 35 or greater as mentioned above. Other epidemiological indications for prenatal diagnostic procedures include family history of a chromosome abnormality and previous pregnancy with a chromosome abnormality.

In 1984, Merkatz and co-workers observed an association between reduced levels of alpha-fetoprotein (AFP) in maternal serum and the likelihood of Down's syndrome pregnancies. This observation has been confirmed by many subsequent studies. In 1987, Bogart and co-worker reported a strong association between elevated maternal serum levels of human chorionic gonadotropin (hCG) and increased likelihood of chromosome abnormalities, particularly Down's syndrome. In pregnancies with fetal trisomy 18 maternal serum hCG levels are usually very low, with most pregnancies having levels less than 0.25 MoM. To date, relative hCG concentration is the most powerful indicator of risk for fetal chromosome abnormality.

In 1988, Canick and co-workers reported an association between low levels of unconjugated estriol (uE3) and pregnancies affected with Down's syndrome. When used in combination with AFP and hCG, uE3 is reported to improve Down's syndrome detection by about 5%. Reduced levels of uE3 have also been reported in pregnancies with fetal trisomy 18.

While the combination of age-related risk and biochemical screening parameters allows for significantly increased detection of fetal chromosome abnormalities, a significant number of pregnancies with fetal chromosome abnormalities are not ascertained. In addition, once it is determined that a pregnant woman is at risk for having a child with a fetal chromosome abnormality, she still will then require the amniocentesis procedure, with its concomitant risks and expense, in order to verify the presence of the abnormality. Improved detection rates could be achieved by increasing the amniocentesis rate, finding more effective biochemical markers or by development of practical methods of analysis of fetal cells that are found in the maternal circulation.

The presence of fetal cells in the maternal circulation has been a matter of scientific interest for many years. Estimates of the number of fetal cells in the maternal circulation range from about 1 in 1000 to 1 in 1,000,000. Efforts to isolate and analyze fetal cells from maternal blood began over 20 years ago. Cells of various types have been identified using morphologic criteria, monoclonal antibodies, and flow cytometry. The cell types identified include fetal lymphocytes, syncytiotrophoblast and fetal erythroblastoid cells. Current efforts at analyzing fetal cells from maternal blood primarily involve flow cytometry combined with molecular genetic technologies such as the polymerase chain reaction or fluorescence in situ hybridization. These techniques suffer from a number of problems and have not achieved practical application.

Direct analysis of fetal lymphocyte chromosomes found in the maternal blood was first reported by Walknowska and co-workers in 1969. By using standard blood culture techniques they reported finding approximately 4 fetal mitosis per 1000 maternal mitosis. They correctly identified 19 male fetuses, missed three males, and misidentified two females as males. They suggest that a 95% accuracy rate could be obtained by analyzing 1200 cells. Unfortunately, such a procedure is prohibitively expensive (about $5000 per patient) and, thus, has not been adopted.

Preferential hemolysis of adult red blood cells has been described by Boyer et al. (1976) and Alter et al. (1979). Unfortunately, most circulating red blood cells do not have a nucleus and, thus, are not useful for chromosome analysis. Occasional nucleated red blood cells may be found in the circulation, particularly in the fetal circulation. These cells, however, do not divide and cannot be used for chromosome analysis.

Taking a different approach, Selypes and Lorencz (1988) proposed a method for obtaining chromosomes from fetal lymphocytes using a technique which involves exposure of the cell culture to the air for 6 hours in order to change the pH of the culture media to approximately 8.0 prior to standard blood culture for 66 hours. They claimed this preferentially stimulated fetal cells to grow such that, on average, 24% of mitotic cells were of fetal origin. Attempts to duplicate their findings have not been successful.

Thus there remains a need for a low cost, safe method for the accurate determination of fetal chromosome abnormalities.

BRIEF SUMMARY OF THE INVENTION

The subject invention concerns a method for detecting and analyzing fetal cells in a maternal blood sample, such as a sample from a pregnant woman. Specifically, the invention concerns a technique for enrichment of the number of fetal lymphocytes undergoing (or capable of undergoing) mitosis in a sample of maternal blood. By enrichment of the number of such fetal lymphocytes, it is possible to isolate these fetal cells from a sample which also contains maternal cells, and to perform chromosome analysis or other evaluation of the fetal cells.

Specifically, the subject invention concerns a method for preferentially and selectively causing a relative increase in the sensitivity of fetal lymphocytes to mitogenic agents. At the same time, this method can preferentially lyse adult red blood cells. Thus, the methods of the subject invention can be used to preferentially stimulate fetal lymphocytes to divide in culture while simultaneously eliminating adult red blood cells and other plasma components. The method thus results in a relative enrichment of fetal cells in blood samples that initially contain a mixture consisting primarily of adult cells.

In a preferred embodiment of the subject invention, maternal erythrocytes and plasma components are removed from a maternal blood sample by dilution and lysis in a solution which will induce erythrocyte lysis without causing significant damage to lymphocytes. The cells are subjected to a shock solution which, in combination with the lysis solution, results in increased lymphocyte response to mitogenic agents. After removal of cellular debris and rinsing in a normal saline solution, the remaining cells can be cultured in the presence of relatively low concentrations of a mitotic stimulant. Standard cytogenetic laboratory techniques are then used to perform chromosome analysis on mitotic cells.

As described herein, a wide variety of chemical solutions can be employed in the lysis procedure, cell separation procedure, and subsequent cell culture so long as the chemical solutions conform to the basic requirements of the method as described herein.

The method is particularly useful for fetal chromosome analysis from blood samples obtained from a pregnant woman. The method of the subject invention advantageously enriches for fetal cells from maternal blood samples and is, therefore, not limited to detecting chromosome disorders. For example, the method can also be used for diagnosis of single gene disorders, as well as other procedures that involve the use of fetal cells.

DETAILED DISCLOSURE OF THE INVENTION

Figure 2:
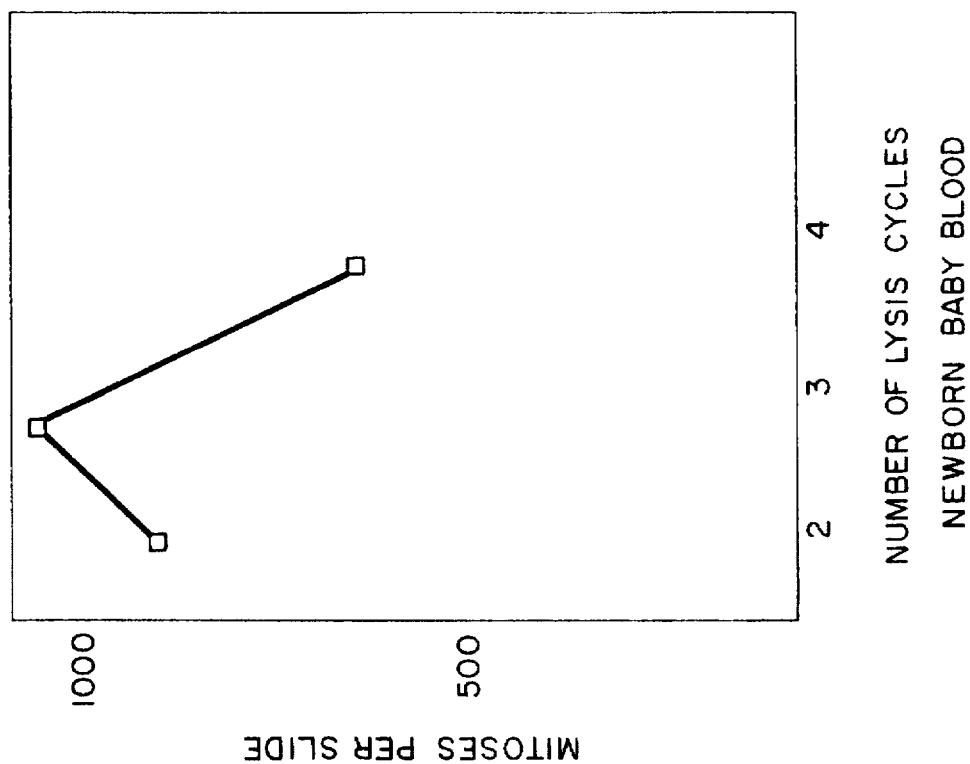
FIG. 2 shows the effect of the number of lysis cycles used in the method on the number of mitotic newborn infant blood cells.

The subject invention concerns materials and methods useful for isolating fetal cells from a sample initially containing a mixture of both fetal cells and adult cells. According to the teachings of the subject invention, a maternal blood sample can be processed so as to enrich for the relatively few fetal cells which may initially be present in such a blood sample. Once the relative number of fetal cells has been increased by the enrichment procedure, it is then possible to use genetic analysis techniques to evaluate the chromosomal characteristics of the fetal cells.

In a preferred embodiment of thee subject invention, the method presents a way of preferentially increasing the relative proliferative response of, fetal lymphocytes in comparison to adult lymphocytes when exposed to a mitotic stimulant. In one embodiment of the subject invention, the fetal cells will respond to lower concentrations of a mitotic stimulant. While the method of the subject invention can increase both the fetal and adult, lymphocyte response to mitogenic agents, the fetal cells are more strongly affected, resulting in a relative increase in the fetal cells' response. When stimulated with a mitotic agent, the fetal lymphocytes divide in tissue culture and metaphase chromosomes can be analyzed by standard cytogenetic techniques. The experiments described below demonstrate that the selective increased response of fetal lymphocytes to a mitotic agent can be exploited to result in a significant increase in the relative number of fetal cells in mitosis in a mixed adult-fetal blood sample.

The relative reduction of the adult lymphocyte response to mitotic stimulants (in comparison to the fetal lymphocyte response) can be accomplished by exposure of a blood sample to conditions specifically described below. The same conditions can result in erythrocyte lysis and removal of plasma components. Other mechanisms may also account for the relatively reduced response of adult lymphocytes to mitotic stimulation including, but not limited to, lymphocyte lysis.

In one embodiment, the method of the subject invention takes advantage of the differences between fetal and adult lymphocyte response to $NH_4Cl$—$HCO_3^-$—a hypertonic mediated, NaCl-precipitated osmotic shock. Specifically, while both fetal and adult lymphocytes become increasingly sensitive to normal concentrations of mitotic agents after exposure to these solutions, the response of the fetal lymphocytes to reduced concentrations is significantly greater than the response of adult lymphocytes, and results in a relative increase in fetal lymphocyte responsiveness. Therefore, a preferential increased response of fetal lymphocytes to reduced concentrations of a mitotic agent can be induced by exposing a mixture of fetal and adult lymphocytes to appropriate solutions as described herein.

It has also been determined that adult red blood cells can be lysed in a hypertonic solution. When adult red blood cells are lysed by a hypertonic solution as described herein, they release carbonic anhydrase. Unfortunately, the carbonic anhydrase released from the lysed adult red blood cells has been found to inhibit the effect of the hypertonic solution on lymphocytes. Consequently, the process of preferentially increasing fetal lymphocyte response to mitotic agents is reduced or eliminated if it is carried out in the presence of red blood cells because the accompanying lysis of the red blood cells results in the release of carbonic anhydrase. This effect can be overcome ,according to the subject invention by addition of a carbonic anhydrase inhibitor such as acetazolamide. This effect can also be eliminated or reduced by removing red blood cells before exposure of the lymphocytes to these solutions. The red blood cells can be removed by, for example, centrifugation or filtration. Chemical means may also be utilized to selectively remove red blood cells. Thus, one embodiment of the subject invention includes removal of red blood cells prior to modifying the relative response of lymphocytes to mitotic agents. This is a particularly useful procedure for concentrating the lymphocyte portion of a blood sample prior to modifying the lymphocyte response to mitotic agents.

In an alternative embodiment, the modifying of the lymphocyte response to mitotic agents is carried out in the presence of red blood cells but in a manner which controls the effect of the released carbonic anhydrase that occurs with red blood cell lysis. Specifically, acetazolamide or other carbonic anhydrase inhibitors can be included with the hypertonic solution. In the presence of the carbonic anhydrase inhibitor, the modification of the lymphocyte response proceeds even if accompanied by lysis of red blood cells. The viable response-modified lymphocytes can then be separated from the debris of the lysed red blood cells.

The underlying mechanism of the cellular lysis of the maternal red blood cells is one in which the diffusion of $CO_2$ into cells and its intracellular hydration to $HCO_3^-$ is matched by an inward diffusion of $NH_3$ and formation of $NH_4^+$. The ion pairs that are created attract water and the cell eventually bursts. The rate-limiting step in this sequence is the conversion of $CO_2$ to $HCO_3^-$. In the case of red blood cells, the concentration of the enzyme carbonic anhydrase, which catalyzes the conversion of $CO_2$ to $HCO_3^-$, becomes the major determinant of the hemolytic rate. Thus, the rate of reaction can be controlled by addition of acetazolamide, a carbonic anhydrase inhibitor, which preferentially enters the fetal red blood cell, thereby allowing preferential lysis of the adult red blood cell.

In the case of lymphocytes, the conversion of $CO_2$ to $HCO_3^-$ appears to proceed via either a non-catalytic conversion or low activity catalytic conversion which is inhibited by carbonic anhydrase released from lysed red blood cells (the primary reaction occurs outside the lymphocytes). Therefore, removal or inhibition of carbonic anhydrase released by lysed red blood cells allows the reaction within lymphocytes to proceed to the point where addition of a shock solution affects the cells' subsequent response to mitogenic agents. That is, when lymphocytes are in a sample with red blood cells which are being lysed, the modification of the lymphocytes' ability to respond to mitogenic agents does not occur or is reduced unless an effective amount of a carbonic anhydrase inhibitor is added.

Following exposure to the lysis solutions and a saline wash, the isolated fetal lymphocytes can be stimulated to divide in culture by standard tissue culture techniques using appropriate stimulation. This mitotic stimulation may be, for example, stimulation with a relatively low concentration of phytohemagglutinin. The exact concentration necessary for a particular application can be readily determined by one skilled in the art utilizing the techniques provided herein. Chromosome harvest and analysis may then proceed according to standard techniques used for blood chromosome analysis (Barch, 1991).

Thus, according to the teachings of the subject invention, selective modification of the fetal lymphocyte response to mitogenic agents is possible. Subsequent stimulation of the fetal lymphocytes in tissue culture results in cell mitosis for subsequent fetal chromosome analysis. In addition, either stimulated or unstimulated fetal lymphocytes and/or fetal chromosomes can be exposed to various molecular genetic methodologies to probe for specific genetic defects.

In the experiments described below, newborn infant blood and nonpregnant adult blood were used to establish cell reaction parameters and to test mixed cell blood samples reaction parameters. After establishment of parameters, blood samples from pregnant women were used.

In practicing the subject invention, the skilled artisan would recognize that reagents and procedures other than those specifically exemplified herein can be utilized, in accordance with the teachings herein, to effect the desired enrichment of dividing fetal lymphocytes. For example, other reagents can be utilized to accomplish the preferential lysing of maternal red blood cells. Chemicals that function in the same manner and have similar properties as the chemicals specifically exemplified are contemplated for use in the invention. For example, sodium bicarbonate ($NaHCO_3$) may be substituted for ammonium bicarbonate. Cell harvest, slide preparation and G-banding were performed according to standard cytogenetic laboratory techniques for all of the following examples.

The following examples are for illustrative purposes and are not intended to be a delineation of all possible modifications to the technique. All percentages are by weight unless otherwise noted.

Materials and Methods

The following solutions are prepared and filter sterilized. Unless otherwise indicated, all chemicals are commercially available from Sigma Chemical Company (St. Louis, Mo.).

(1) $10^{-2}$M acetazolamide was prepared in 0.15N NaOH (0.22 g acetazolamide/100 ml of 0.15N NaOH) and the pH adjusted to 6.8 with glacial acetic acid.

(2) 0.15M NaCl (0.876 g/100 ml $H_2O$).

(3) Ammonium bicarbonate, 30 mM $NH_4HCO_3$ (0.237 g/100 ml $H_2O$).

(4) Ammonium chloride, 0.1844M $NH_4Cl$ (0.986 g/100 ml $H_2O$).

(5) Shock solution, 1.8% NaCl.

(6) Double concentration shock solution, 3.6% NaCl.

(7) Phosphate buffered saline (PBS), 1 Gurr pH 6.8 buffer tablet (Bio/medical Specialties, Santa Monica, Calif.) dissolved in 0.9% NaCl.

Reagent mix. One milliliter of the $10^{-2}$M acetazolamide solution was added to 9 ml of 0.15M NaCl and 90 ml of 0.1844M NH$_4$Cl. This solution designated herein as the "reagent mix." The same solution minus the 1 ml of acetazolamide solution is designated "reagent mix-minus-acetazolamide." Carbonic anhydrase inhibitors other than acetazolamide can also be used in the "reagent mix."

Tissue culture media. Any tissue culture media suitable for lymphocyte culture is suitable for the cell culture portion of the methods described herein. Tissue culture media was prepared as follows: 100 ml of RPMI 1640 (Hepes buffered) plus 1 ml antibiotic-antimycotic, 15 ml fetal calf serum, and 1 ml L-glutamine (200 mM). These products were purchased from Grand Island Biological Corporation (Gaithersburg, Md.). Leucoagglutinin (PHA-L) (Sigma or Grand Island Biological Corporation) was added to the culture media to stimulate lymphocyte growth. Other mitogenic agents, such as phytohemagglutinin (PHA-M or PHA-P), pokeweed mitogen, and lipopolysaccharide (LPS), can also be used. PHA-L was used at a concentration of about 5 µg/ml in the following examples. However, because PHA potency varies from batch to batch, each batch should be tested to determine the concentration that gives optimal stimulation of fetal lymphocytes over adult lymphocytes. "FICOLL-PAQUE" was purchased from Pharmacia Inc. (Piscataway, N.J.). "FICOLL-PAQUE" is a non-ionic synthetic polymer of sucrose.

EXAMPLE 1

Multiple Cycle Methodology for Lysis of Maternal Cells

Initially, 10 ml of reagent mix is added to 0.5 ml of adult blood. After 2 minutes, 2 ml of ammonium bicarbonate solution is added. After 4 minutes a volume of shock solution is added that is approximately equal to the total volume of the other reagents. The sample is centrifuged at 1500 rpm for 10 minutes. This constitutes one lysis cycle. The supernatant is removed and 10 ml of reagent mix is added to the remaining material for 2 minutes, then 2 ml of ammonium bicarbonate solution is added. After 4 minutes, shock solution is added as before. The procedure is repeated for a total of 4 lysis cycles. After the final centrifugation, the supernatant is removed and replaced with 10 ml of PBS. The solution is mixed and then centrifuged again. After the PBS rinse supernatant is removed, the remaining cell pellet is cultured in tissue culture media according to standard techniques in the presence of a mitogenic agent such as phytohemagglutinin.

Figure 1:
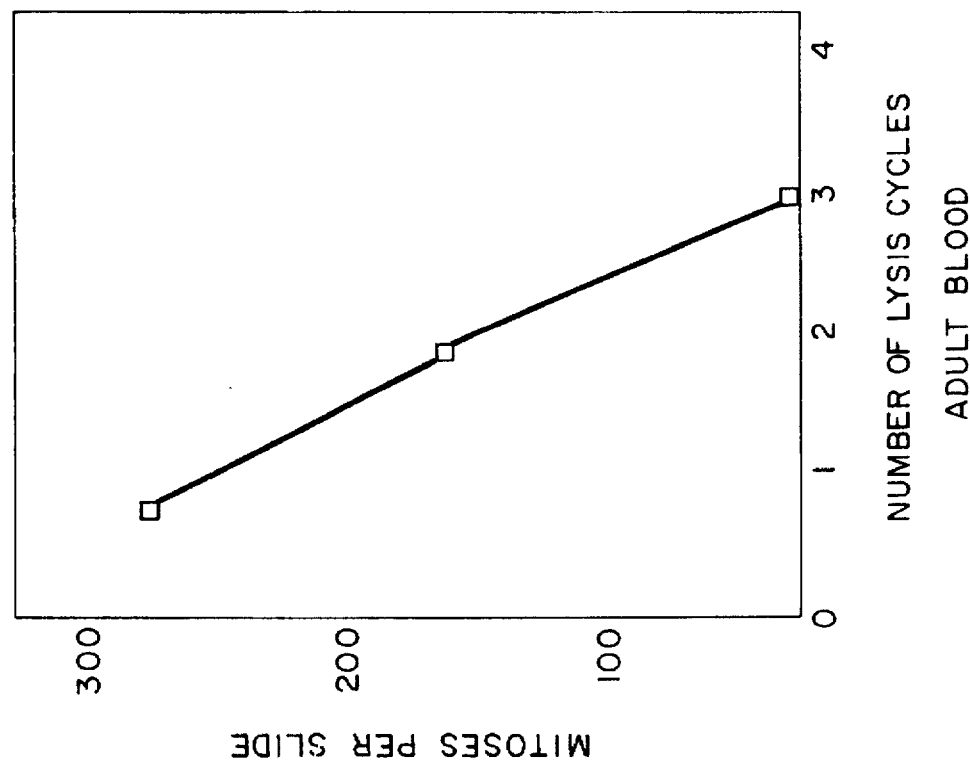
FIG. 1 shows the effect of the number of lysis cycles used in the method on the number of mitotic adult blood cells.

When 0.5 ml of adult blood was subjected to these procedures the results showed a significant reduction in the number of mitotic cells after two lysis cycles. No mitotic cells could be detected after 3 lysis cycles (FIG. 1). By contrast, when 0.5 ml of newborn baby blood was subjected to the same experimental conditions the results showed no significant reduction in the number of mitotic cells after 4 lysis cycles (FIG. 2).

As an alternative to initially adding 10 ml of reagent mix to 0.5 ml of adult blood, 10 ml of blood can be centrifuged at about 1000 rpm for 10 minutes, the plasma layer removed, and the top 2 ml of the remaining pellet containing the "buffy coat" layer transferred to a tube containing 10 ml of the reagent mix. The procedure would then continue as described above.

EXAMPLE 2

Importance of Shock Solution

One half millimeter of adult blood was subjected to the method described in Example 1 above except that the addition of the shock solution was eliminated from the procedure. These results were compared to those obtained when the shock solution was included in the procedure.

Figure 3:
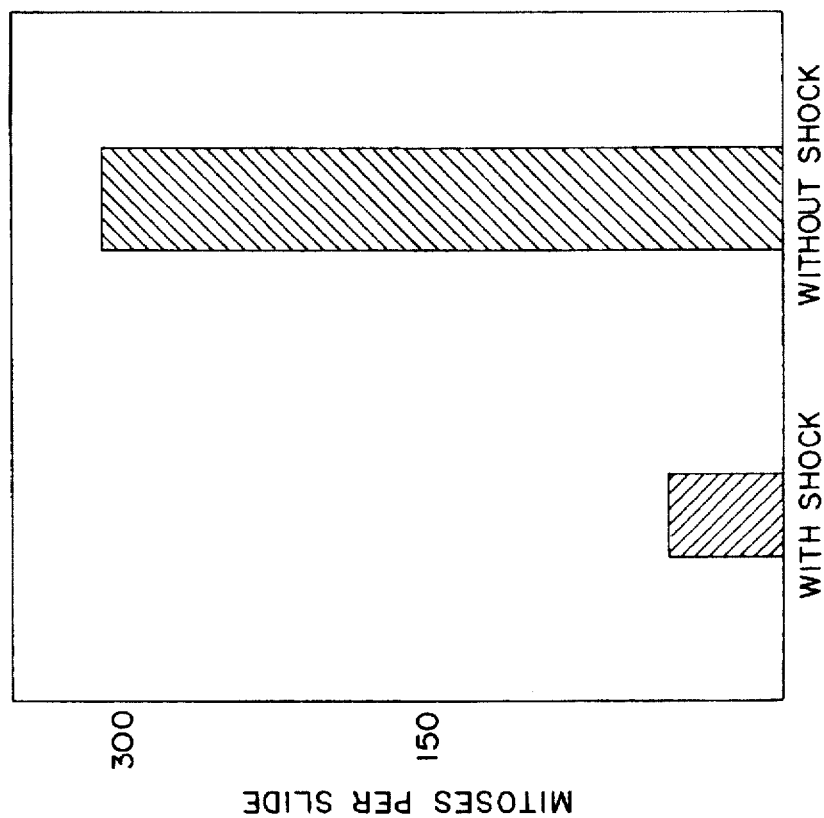
FIG. 3 shows the effect of the saline shock solution on the number of mitotic adult blood cells.

Results showed approximately 8 times as many mitotic cells per slide when the shock solution was not included in the method (FIG. 3). Thus, the shock solution plays a critical role in reducing the number of mitotic adult cells.

EXAMPLE 3

Substitution with Sodium Bicarbonate

Adult blood (0.5 ml) was subjected to the method as described in Example 1 except that sodium bicarbonate solution was substituted for the ammonium bicarbonate solution.

Figure 4:
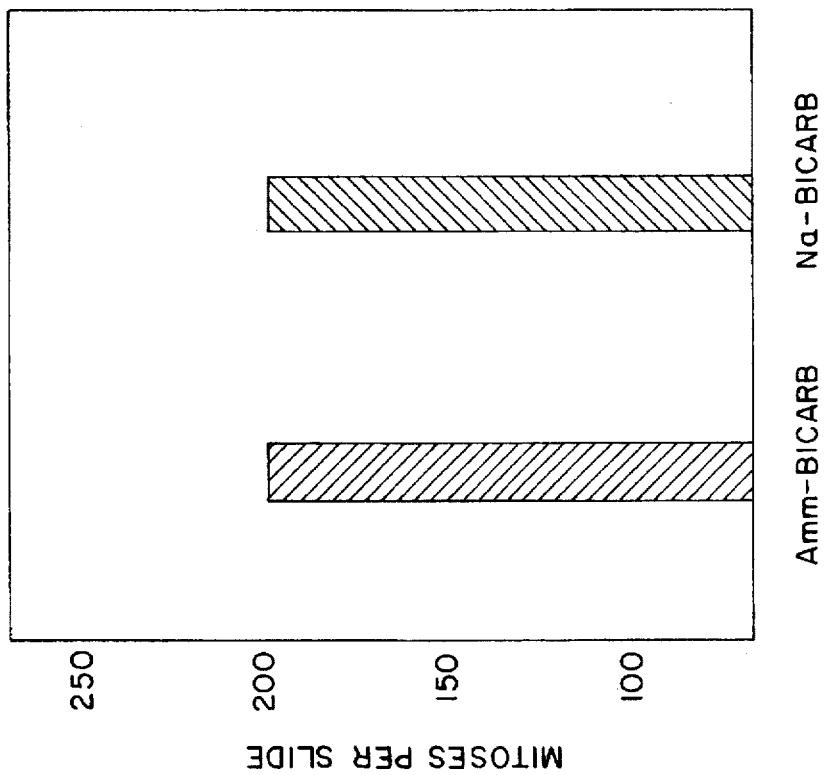
FIG. 4 shows a comparison between the effects of ammonium bicarbonate solution and sodium bicarbonate solution using the standard method on the number of mitotic adult blood cells.

Results showed no difference in mitotic index when either solution was used in the method (FIG. 4).

EXAMPLE 4

Single Step Methodology for Lysis of Maternal Cells

An alternative to the multiple lysis cycle method illustrated in Example 1 is a single step lysis procedure that involves a longer incubation of cells in the reagent mix-ammonium bicarbonate solution. Initially, 10 ml of reagent mix is added to 0.5 ml of blood. After 2 minutes, 2 ml of ammonium bicarbonate solution is added. After addition of the ammonium bicarbonate solution the sample is allowed to stand at room temperature for 25–40 minutes, followed by the addition of a volume of shock solution equal to the total volume of the other added solutions. The sample is then centrifuged at 1500 rpm for 10 minutes, and the supernatant removed. The procedure then continues as in Example 1 with the PBS rinse step.

Results using adult cells showed significant reduction in the number of mitotic cells detected with increasing lysis time such that there were 125 mitotic cells per slide at 25 minutes, 8 mitotic cells per slide at 30 minutes, 1 mitotic cell per slide at 35 minutes and no mitotic cells detected at 40 minutes.

EXAMPLE 5

Importance of Acetazolamide

One-half milliliter of blood from an adult was subjected to the method described in Example 4 above except that the acetazolamide solution was not included the reagent mix solution. This was compared to the results obtained using reagent mix containing acetazolamide.

Figure 5:
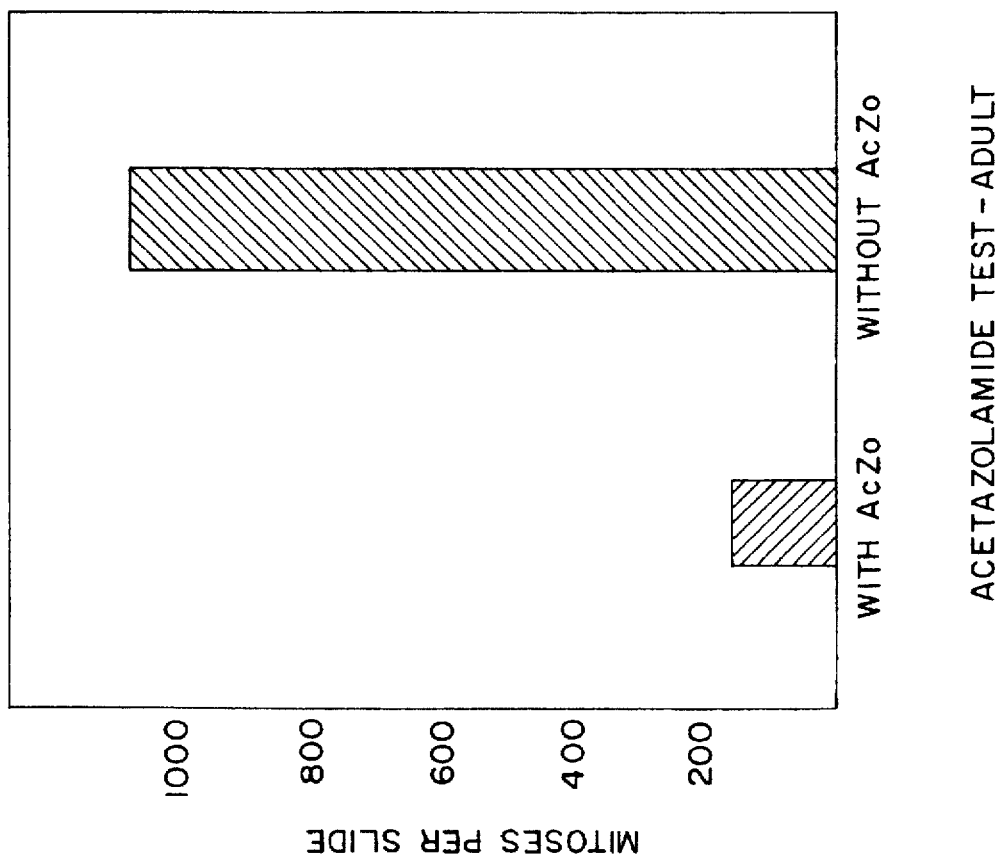
FIG. 5 shows the effects of acetazolamide on the number of mitotic adult blood cells.

Results showed significantly more mitoses after a single 30 minute lysis step in the procedure without acetazolamide in comparison to the procedure with acetazolamide. Results from adult blood are shown in FIG. 5. This indicates acetazolamide is necessary for an efficient reduction in the number of adult lymphocyte mitoses.

EXAMPLE 6

Acetazolamide Concentration

Blood from an adult or newborn infant (0.5 ml) was subjected to the method as described in Example 4. In addition, 0.5 ml samples of blood were subjected to the method as described in Example 4 except that the concentration of the acetazolamide solution in the reagent mix was doubled or quadrupled.

Results with newborn infant blood showed that increasing concentrations of acetazolamide are inversely correlated with mitotic index. A leveling-off of mitotic index (as determined by the number of mitoses per slide) was observed as complete carbonic anhydrase inhibition was approached.

EXAMPLE 7

Methodology for Large Volumes of Maternal Blood

In one embodiment of the subject invention, 6 to 10 ml of whole maternal blood can be added to 35 ml of reagent-mix-minus-acetazolamide for 2 minutes. Seven milliliters of ammonium bicarbonate solution is then added and the mix allowed to stand for 10 minutes. After centrifugation at about 1500 rpm for 10 minutes the supernatant is removed and 20 ml of reagent mix is added. After 2 minutes, 4 ml of ammonium bicarbonate is added. After 4 minutes, 24 ml of shock solution is added. The procedure continues as described in Example 1 for a total of 3 or 4 lysis cycles (or as described in Example 4 for a single 30–40 minute cycle). After the final spin, but prior to the PBS rinse, approximately 4 ml of the remaining cell suspension is layered on 3 ml of "FICOLL-PAQUE" and centrifuged for 30 minutes at about 2000 rpm. The lymphocyte layer is removed and washed twice in 10 ml PBS prior to cell culture.

EXAMPLE 8

Alternate Method for Large Volumes of Maternal Blood

Six to ten milliliters of whole maternal blood is added to 35 ml of reagent mix for 2 minutes. Seven milliliters of ammonium bicarbonate solution is then added and the mix allowed to stand for 4 minutes. Twenty-four milliliters of double concentration shock solution (3.6% NaCl) is added and the solution is then centrifuged at 1500 rpm for 10 minutes. The supernatant is removed and 20 ml of reagent mix is added. After 2 minutes, 4 ml of ammonium bicarbonate is added. After 4 minutes, 24 ml of shock solution (1.8% NaCl) is added. The solution is centrifuged and the procedure continues for a total of 3 or 4 lysis cycles. Cells are then washed once in PBS prior to cell culture in the presence of a mitogenic agent.

A specific embodiment of the above alternate method, adapted for ease of use in a laboratory, is shown below:

1. Add 6 ml of maternal blood to 25 ml of reagent mix in 50 ml centrifuge tube. Mix and wait 2 minutes.
2. Add 5 ml of ammonium bicarbonate. Mix and wait 4 minutes.
3. Add 15 ml of double strength shock solution.
4. Centrifuge for 10 minutes at 1500 rpm.
5. Remove supernatant and add 20 ml of reagent mix. Mix and wait 2 minutes.
6. Add 4 ml ammonium bicarbonate. Mix and wait 4 minutes.
7. Add 24 ml shock solution and mix.
8. Centrifuge for 6 minutes at 1000 rpm.
9. Repeat steps 5, 6, 7, and 8.
10. Remove supernatant and re-suspend cells in 10 ml of phosphate-buffered normal saline (PBS).
11. Centrifuge for 6 minutes at 1000 rpm.
12. Remove supernatant and re-suspend cells in blood culture media with PHA.
13. Culture cells for 68–72 hours and harvest according to standard blood harvest procedure.

EXAMPLE 9

Differential Effect on Newborn and Adult Blood

Newborn infant blood (0.02 ml) was added to 3 ml of adult blood. One-half milliliter of the baby-adult blood mix was subjected to the method described in Example 1 above.

Results showed twice as many mitotic infant cells as mitoic adult cells after 3 lysis cycles.

EXAMPLE 10

Application of Methodology to Maternal Blood

Blood from a pregnant woman (6 ml) was subjected to the method as described in Example 8. Results showed a ratio of fetal to maternal mitotic cells of 3 to 4. This reflects a relative enhancement of the fetal mitotic cells.

EXAMPLE 11

Effect of PHA Concentration

Blood from a pregnant woman was subjected to the method as described in Example 10 except that the cells were exposed to various concentrations of PHA-L.

Results showed an increasing number of maternal mitosis with increasing PHA-L concentration. At low concentrations of PHA-L the fetal cells remain able to be stimulated, whereas the maternal cells are unresponsive. At high concentrations of PHA-L the total number of maternal mitosis exceeds that obtained without exposure of the blood to the lysis cycles. Thus, the procedure appears to increase the number of cells able to respond to PHA-L stimulation (as determined by increased numbers of cells in mitosis) and that this effect is more pronounced for fetal cells than for adult cells. This results in preferential stimulation of fetal cells at reduced concentrations of PHA-L.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Barch, M. J. (ed.) (1991) *The ACT Cytogenetics Laboratory Manual*, Raven Press, New York.

Bogart, M. H., M. R. Pandian, O. W. Jones (1987) "Abnormal maternal serum chorionic gonadotropin levels in pregnancies with fetal chromosome abnormalities," *Prenat. Diagn.* 7:623–630.

Boyer, S. H., A. N. Noyes, M. L. Boyer (1976) "Enrichment of Erythrocytes of Fetal Origin From Adult-Fetal Blood Mixtures via Selective Hemolysis of Adult Blood Cells: An Aid to Antenatal Diagnosis of Hemoglobinopathies," *Blood* 47:883–897.

Bianchi, D. W., S. Sylvestar, G. K. Zickwolf, M. A. DeMaria, G. J. Weil, O. H. Galfman (1993) "Fetal stem cells persist is maternal blood for decades post-partum," *Am. J. Hum. Genet* 53(3 supplement):251.

Canick, J. A., G. J. Knight, G. E. Palmaki, J. E. Haddown, H. S. Chuckle, N. J. Wald (1988) "Low second trimester maternal serum unconjugated oestriol in pregnancies with Down's's syndrome," *Br. J. Obstet. Gynecol.* 95:330–333.

Ganiats, T. G., A. L. Halverson, M. H. Bogart (1994) "Marginal cost-effectiveness of incorporating estriol evaluation in Down's syndrome screening programs," *Prenat. Diagn.* (in press).

Hamada, H., T. Arinami, T. Kubo, H. Hamaguchi, H. Iswsaki (1993) "Fetal nucleated cells in maternal peripheral blood: frequency and relationship to gestational age," *Hu. Genet.* 91:427–432.

Merkatz, I. R., H. M. Nitowsky, J. N. Macri, W. J. Johnson (1984) "An association between low maternal serum alpha-fetoprotein and fetal chromosome abnormalities," *Am. J. Obstet. Gynecol.* 148:886–894.

President's Commission for the Study of Ethical Problems in Medicine and Biomedical and Behavioral Science (1983) "Screening and Counseling for Genetic Conditions," U.S. Government Printing Office, Washington D.C.

Selypes, A., R. Lorencz (1988) "A noninvasive method for determination of the sex and karyotype of the fetus from the maternal blood," *Hum. Genet.* 79:357–359.

Walknowska, J., F. A. Conte, M. M. Grumbach (1969) "Practical and theoretical implications of feta/maternal lymphocyte transfer," *Lancet* 1:119–1122.

I claim:

1. A method for enriching fetal lymphocytes relative to other cells in a maternal blood sample, comprising the steps of:

(a) removing erythrocytes from the maternal blood sample, leaving a cell suspension comprising fetal and maternal lymphocytes;

(b) treating the cell suspension obtained from step (a) with a hypertonic shock solution in an amount sufficient to cause the cells to be subjected to hypertonic conditions, thereby preferentially conditioning fetal lymphocytes in the cell suspension to undergo mitotic division; and (c) adding a mitotic stimulant to stimulate the fetal lymphocytes to undergo mitotic division at a rate greater than the maternal lymphocytes in culture by exposing the cell suspension to a concentration of a mitotic stimulant sufficient to stimulate the rate of mitotic division in a major fraction of fetal lymphocytes and insufficient to stimulate the rate of mitotic division in a major fraction of maternal lymphocytes; and allowing the lymphocytes to divide.

2. The method, according to claim 1, further including the step of separating fetal lymphocytes from the cell suspension obtained from step (b) by density gradient centrifugation.

3. The method, according to claim 1, further including the step of repeating steps (b) and (c) 3 to 4 times prior to proceeding to step (d).

4. The method of claim 1, wherein the mitotic stimulant is selected from the group consisting of leucoagglutinin, pokeweed mitogen, phytohemagglutinin and lipopolysaccharide.

5. The method, according to claim 1, wherein step (a) is the step of centrifuging the maternal blood sample to separate the erythrocytes from the maternal blood sample.

6. A method for selecting and culturing fetal lymphocytes from a maternal blood sample, comprising the steps of:

(1) adding a reagent solution comprising sodium chloride, ammonium chloride, and carbonic anhydrase inhibitor to obtain a cell suspension;

(2) adding a bicarbonate solution selected from the group of ammonium bicarbonate and sodium bicarbonate to the cell suspension and reacting the cell suspension with the bicarbonate solution for about four minutes in order to lyse erythrocytes;

(3) adding a sodium chloride shock solution to the reacted cell suspension;

(4) centrifuging the reacted cell suspension;

(5) sequentially treating a cell pellet obtained from step (4) with
   i) the reagent solution of step (1);
   ii) ammonium bicarbonate solution; and
   iii) a sodium chloride shock solution in an amount sufficient to condition fetal lymphocytes to undergo mitotic division, thereby yielding a treated cell suspension;

(6) centrifuging the treated cell suspension;

(7) washing a cell pellet obtained from step (6) in a phosphate buffered saline wash solution; and (8) culturing fetal lymphocytes present in the washed cell pellet obtained from step (7) in the presence of a sufficient concentration of a mitotic stimulant to induce mitotic division of the fetal lymphocytes and allowing the lymphocytes to divide.

7. The method of claim 6, wherein step (5) further comprises the steps of treating the cell pellet obtained from step (4) by reacting the cell pellet with the reagent solution of step (1) for about two minutes, then adding the ammonium bicarbonate solution and reacting for about four minutes, and adding a volume of the sodium chloride shock solution in a volume approximately equal to the total volumes of reagent solution and ammonium bicarbonate solution.

8. The method of claim 6, further comprising the step of repeating steps 4 and 5 about one to two additional times prior to proceeding to step (6).

9. A method for enriching the fetal lymphocyte population relative to other cells in a maternal blood sample, comprising the steps of:

(a) lysing erythrocytes in the maternal blood sample by adding a solution comprising ammonium chloride, ammonium bicarbonate and carbonic anhydrase inhibitor in an amount sufficient to preferentially lyse erythrocytes in the blood sample;

(b) adding a hypertonic salt solution to the remaining cells in the blood sample which comprises the fetal lymphocytes in an amount sufficient to cause the cells to be subjected to hypertonic conditions;

(c) adding a mitogenic stimulant to the remaining cells in an amount sufficient to cause the fetal lymphocytes to divide more rapidly than the maternal lymphocytes and;

(d) allowing the lymphocytes to divide.

10. The method, according to claim 9, wherein said carbonic anhydrase inhibitor is acetazolamide.

11. The method of claim 9, wherein the mitotic stimulant is selected from the group consisting of leucoagglutinin, pokeweed mitogen, phytohemagglutinin and lipopolysaccharide.

* * * * *